(12) United States Patent
Ymeti et al.

(10) Patent No.: US 8,792,103 B2
(45) Date of Patent: Jul. 29, 2014

(54) SYSTEM FOR ANALYSIS OF A FLUID

(75) Inventors: Aurel Ymeti, Enschede (NL); Paulus Hendricus Johannes Nederkoorn, Enschede (NL); Johannes Sake Kanger, Hengelo (NL); Alma Dudia, Enschede (NL); Vinod Subramaniam, Enschede (NL)

(73) Assignee: Ostendum Holding B.V., Enschede (NL)

( * ) Notice: Subject to any disclaimer, the term of this patent is extended or adjusted under 35 U.S.C. 154(b) by 41 days.

(21) Appl. No.: 13/147,545

(22) PCT Filed: Feb. 4, 2010

(86) PCT No.: PCT/NL2010/000018
§ 371 (c)(1),
(2), (4) Date: Oct. 7, 2011

(87) PCT Pub. No.: WO2010/090514
PCT Pub. Date: Aug. 12, 2010

(65) Prior Publication Data
US 2012/0019833 A1    Jan. 26, 2012

(30) Foreign Application Priority Data

Feb. 4, 2009    (NL) .................................... 2002491

(51) Int. Cl.
*G01B 9/02*    (2006.01)
(52) U.S. Cl.
USPC ........................................ 356/477; 356/481
(58) Field of Classification Search
CPC ............. G01N 21/45; G01N 21/7703; G01N 2021/458; G01N 2021/7779; G02B 6/2813
USPC ........................................ 356/477–483, 517
See application file for complete search history.

(56) References Cited

U.S. PATENT DOCUMENTS

| | | | | |
|---|---|---|---|---|
| 4,950,074 A | * | 8/1990 | Fabricius et al. | 356/133 |
| 5,120,131 A | * | 6/1992 | Lukosz | 356/481 |
| 5,262,842 A | * | 11/1993 | Gauglitz et al. | 356/477 |
| 5,377,008 A | * | 12/1994 | Ridgway et al. | 356/481 |
| 5,465,151 A | * | 11/1995 | Wybourne et al. | 356/481 |

(Continued)

FOREIGN PATENT DOCUMENTS

WO    WO 2004020987 A1 *  3/2004

OTHER PUBLICATIONS

Ymeti, Aurel et al., Development of a multichannel integrated interferometer immunosensor, Sensors and Actuators B, Elsevier, vol. 83 (2002), pp. 1-7.*

(Continued)

*Primary Examiner* — Michael A Lyons
(74) *Attorney, Agent, or Firm* — McGuireWoods, LLP

(57) ABSTRACT

A system for analysis of a fluid, comprises a light source for radiating a beam of light an optical path for guiding at least part of the beam of light, a fluidic channel for guiding the fluid along the optical path, and a detector for detecting an optical characteristic of the light having propagated along the optical path. The optical path comprises a multimode interference structure, the multimode interference structure being arranged for providing a propagation of the beam of light in at least two propagation modes, the detector being positioned so as to receive light from each of the at least two propagation modes.

15 Claims, 3 Drawing Sheets

(56) References Cited

U.S. PATENT DOCUMENTS

Figure 1:
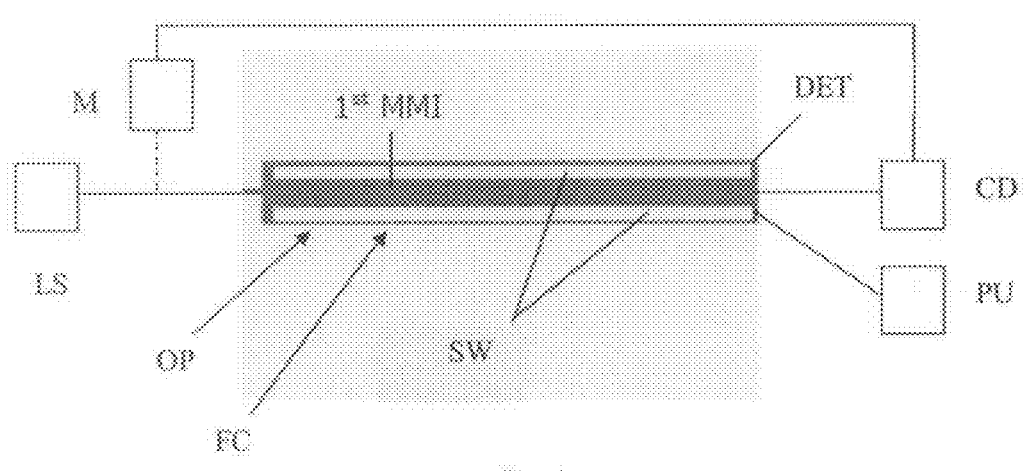

| | | | |
|---|---|---|---|
| 6,016,197 A * | 1/2000 | Krivoshlykov | 356/451 |
| 6,130,439 A * | 10/2000 | Le Menn | 250/573 |
| 6,137,576 A * | 10/2000 | Pauluth et al. | 356/517 |
| 6,239,876 B1 * | 5/2001 | Brandenberg | 356/481 |
| 6,330,064 B1 * | 12/2001 | Rieder | 356/481 |
| 6,335,793 B1 * | 1/2002 | Freeman et al. | 356/477 |
| 6,429,023 B1 * | 8/2002 | Gharavi | 436/167 |
| 6,483,959 B1 * | 11/2002 | Singh et al. | 385/12 |
| 7,050,176 B1 * | 5/2006 | Cross et al. | 356/517 |
| 7,062,110 B2 * | 6/2006 | Freeman et al. | 385/12 |
| 7,254,291 B2 * | 8/2007 | Burie et al. | 385/14 |
| 8,279,445 B2 * | 10/2012 | Dominguez Horna et al. | 356/477 |
| 2002/0122615 A1 * | 9/2002 | Painter et al. | 385/15 |
| 2004/0004180 A1 * | 1/2004 | Freeman et al. | 250/227.14 |
| 2004/0257579 A1 * | 12/2004 | Shirai et al. | 356/477 |
| 2005/0009196 A1 * | 1/2005 | Freeman et al. | 436/149 |
| 2005/0162659 A1 * | 7/2005 | Freeman et al. | 356/477 |
| 2005/0163413 A1 * | 7/2005 | Freeman et al. | 385/12 |
| 2005/0254744 A1 * | 11/2005 | Freeman | 385/12 |
| 2007/0110363 A1 * | 5/2007 | Miyadera et al. | 385/27 |
| 2011/0292398 A1 * | 12/2011 | Klein Koerkamp et al. | 356/477 |
| 2012/0024571 A1 * | 2/2012 | Freeman et al. | 174/126.1 |

OTHER PUBLICATIONS

Ymeti, Aurel et al., Fast, Ultrasensitive Virus Detection Using a Young Interferometer Sensor, Nano Letters, vol. 7, No. 2 (2007), pp. 394-397.*
Ymeti, Aurel et al., Integration of microfluidics with a four-channel integrated optical Young interferometer immunosensor, Biosensors and Bioelectronics, vol. 20 (2005), pp. 1417-1421.*
Ymeti, Aurel et al., Realization of a multichannel integrated Young interferometer chemical sensor, Applied Optics, vol. 42, No. 28 (Oct. 1, 2003), pp. 5649-5656.*
Campbell, Daniel P., Interferometric Biosensors, Principles of Bacterial Detection: Biosensors, Recognition Receptors and Microsystems, Springer (2008), pp. 169-211.*
Copperwhite, Robert, Characterisation of Novel Refractometric Sensing Systems, Advanced Environmental, Chemical, and Biological Sensing Technologies III, Proc. of SPIE, vol. 5993, 59930E-1 (2005).*
Cross et al., Dual Polarization Interferometry: A Real-Time Optical Technique for Measuring (Bio)molecular Orientation, Structure and Function at the Solid/Liquid Interface, Handbook of Biosensors and Biochips, Wiley (2007), pp. 1-20.*
Kim, Daeik D. et al., Integrated Mixed-signal Optoelectronic System-on-a-Chip Sensor, IEEE, (2005), pp. 1738-1741.*
Wang et al., Integrated dual-slab waveguide interferometer for glucose concentration detection in the physiological range, Optical Sensors, SPIE vol. 7003 (2008), pp. 1-10.*
Kribich et al., Novel chemical sensor/biosensor platform based on optical multimode interference (MMI) couplers, Sensors and Actuators B, vol. 107 (2005), pp. 188-192.*
Bornhop et al. (Bornhop, Darryl J. et al., Free-Solution, Label-Free Molecular Interactions Studied by Back-Scattering Interferometry, Science 317, 1732 (2007), pp. 1732-1736.*
International Search Report for PCT/NL2010/000018, mailed on related PCT application, Apr. 22, 2010.
Copperwhite, R., et al. : "Characterisation of Novel Refractometric Sensing Systems" Proceedings of the SPIE—The International Society for Optical Engineering, vol. 5993, No. 1, Nov. 9, 2005.
Kribich, K.R., et al. : "Novel Chemical Sensor/Biosensor Platform Based on Optical Multimode Interference (MMI) Couplers" p. 188-192, (2005).
Kim, Daeik D, et al. "Integrated Mixed-Signal Optoelectronic System-On-A-Chip Sensor" Proceedings—IEEE International Symposium on Circuits and Systems 2005; pp. 1738-1741.
May-Arrioja D.A., et al. "A Reconfigurable Multimode Interference Splitter for Sensing Applications" Measurement Science and Technology, IPO Publishing; vol. 18 No. 10, Sep. 12, 2007 pp. 3241-3246.
Mazingue, Thomas et al. "Chemical Sensors based on optical sensitivity of metal oxide materials deposited on multimode interference couplers" Proceeds of the SPIE—The International Society for Optical Engineering USA; vol. 6785 Aug. 20, 2007 pp. 67850G-1-67850G-7.
Mazingue, T., et al. "Simulations of Refractive Index Variation in a Multimode Interference Coupler: Application to Gas Sensing" Optics Communications, North-Holland Publishing Co. Amsterdam, NL; vol. 278, No. 2 pp. 312-316, (2007).
Wang, Qian, et al. "All-Fiber Multimode-Interference-Based Refactometer Sensor: Proposal and Design" Optics Letters Opt. Soc. America USA; vol. 31, No. 3; Feb. 1, 2006 pp. 317-317.

* cited by examiner

SYSTEM FOR ANALYSIS OF A FLUID

CROSS-REFERENCE TO RELATED APPLICATIONS

This application is a National Stage entry under 35 U.S.C. §371 of International Patent Application No. PCT/NL2010/000018, published as WO 2010/090514, filed on Feb. 4, 2010, which claims priority of Netherlands Patent Application No. NL2002491, filed on Feb. 4, 2009. The disclosures of PCT/NL2010/000018 and NL2002491 are hereby incorporated herein by reference in their entirety.

The invention relates to a system for analysis of a fluid.

EP-A-1 000 342 discloses a detector device having an interferometer. A light beam is split in a measurement beam guided along a measurement path and a reference beam guided along a reference part. A fluid to be tested is guided along the measurement part, thereby the fluid interacting with the light propagating through the measurement part. The measurement beam having propagated along the measurement path and the reference beam having propagated along the reference path, are formed into divergent light beams which interfere and overlap, and form an interference pattern on a detector, such as a CCD array. Information regarding e.g. a property or composition of the fluid (which effects a propagation characteristic of the light in the measurement path), can be derived from the interference pattern as detected by the detector.

In this approach, an optical divider is provided to divide the light into a beam for the measurement path and a beam for the reference path. The optical divider may result in losses of optical energy, and/or alignment problems as both the measurement and the reference path require to be aligned with the respective output channels of the divider. In an attempt to address such problems, a planar structure having an integrated optical divider is proposed in A. Brandenburg et. al., Integrated optical young interferometer, Applied Optics, 33(25), 5941-5947, (Jan. 9, 1994). This solution however results in an increase in dimensions of the planar structure, which increases a cost thereof, and may nevertheless result in optical losses.

An object of the invention is to provide an alternative to the above solutions.

In order to achieve this object, the system according to an aspect of the invention comprises:
a light source for radiating a beam of light
an optical path for guiding at least part of the beam of light,
a fluidic channel for guiding the fluid along the optical path, and
a detector for detecting an optical characteristic of the light having propagated along the optical path,
wherein the optical path comprises a multimode interference structure, the multimode interference structure being arranged for providing a propagation of the beam of light in at least two propagation modes, the detector being positioned so as to receive light from each of the at least two propagation modes.

The multimode interference structure provides for a propagation of the light in different propagation modes. Along the propagation path, a measurement region and a reference region are provided. Interaction of one or more of the modes of the light (e.g. by a binding of a particle in the fluid with an antibody (or with another receptor) provided along the measurement region), at least in the measurement region provides for a change in propagation of at least one of the modes, and may provide for a change in the interference between the modes. As a result, a change in the light pattern as provided by the different modes onto the detector may occur, hence allowing to detect a propagation characteristic by an analysis of the pattern provided onto the detector resulting from the different optical propagation modes, propagations thereof and interferences there between, thereby obviating the need for an optical divider, as instead of a separation of the beam into a measurement and reference beam, different optical modes of only a single beam are used.

The fluidic channel may comprise at least two sensing windows to allow the light to interact with the fluid, one of the sensing windows to act as a measurement region, the other to act as a reference region. Thereby, a stable and accurate measurement may be provided, as small differences between the measurement and reference may result in changes in the pattern onto the detector, which may be detected.

The sensing windows may extend in parallel along a direction of propagation of the light in the multimode interference structure, to thereby provide an optimum sensitivity as the effects of the sensing windows on the propagation of the light extend along the length of the propagation window.

To detect a specific analyte particle (e.g. a molecule, molecule group, virus, bacterium, cell, biomarker, protein, or others), an antibody, such as a specific antibody, or other receptor may be provided along the sensing window which is to act as the measurement region.

The multimode interference structure may be arranged to allow the at least two propagation modes to propagate in a pattern of lateral minima and maxima, a propagation length of the first multimode interference structure being dimensioned so as to provide a lateral maximum at its end. Thereby an optimum sensitivity may be provided. The detector may be positioned at an end of the multimode interference, so as to provide the light from the at least two propagation modes onto the detector in a spatially distributed manner. By positioning the detector substantially directly at the end of the multimode interference structure, an air medium or other medium for propagation towards the detector may at least partially be omitted, which may result in an improvement of the interference pattern stability, which further may contribute in an improvement of the measurement stability, hence possibly a lower drift, better accuracy and higher sensitivity. Also, scattering losses at an endface of the multimode interference structure may be suppressed, which may result in an additional improvement of the interference pattern stability.

Instead of positioning the detector at the end of the multimode interference structure, a further multimode interference structure may be provided which is positioned downstream of the multimode interference structure, the further multimode interference structure having a width exceeding a width of the multimode interference structure to provide multiple propagation modes in the further multimode interference structure, an interference pattern between the multiple propagation modes to be detected by the detector. The second multimode interference structure may provide for a generation of more propagation modes than in the first multimode interference structure, hence providing interference between these modes in the further multimode interference structure, which may result in an increased measurement sensitivity. In this configuration, in addition to the measurement of the interference pattern, the possibility is offered to measure the intensity distribution change in the second multimode interference structure. This can provide alternative/additional information about the binding events, and may even result in an increased sensitivity.

The light source may comprise a single mode light beam source. The light beam can comprise of one or more separate wavelengths or a wavelength spectrum. Preferably, the light beam is centered and having a Gaussian field profile. Thereby, it may be provided that only symmetric modes are excited in the first multimode interference structure When symmetric modes are excited, a symmetric field distribution along the MMI structure may be provided, which may be preferable in selecting a measurement region and a reference region that are positioned symmetrically along the multimode interference structure.

Other solutions are possible too, e.g. coupling two or more light beams each having a different wavelength and/or polarization into the multimode interference structure. Use of a plurality of wavelengths and/or polarizations (which are e.g. intermittently detected by means of suitable, periodically changing filters) could be used to provide additional information about the binding events. This additional information can be used e.g. to measure/estimate the non-specific binding that may occur when a complex sample such as body fluid (serum, blood, etc) milk, etc has to be analyzed. This may result in an improved accuracy and sensitivity.

The multimode interference structure may be provided in a chip, hence resulting in a compact, low cost measurement structure. The chip may further comprise the detector, which may avoid coupling losses of coupling the light to the detector.

A processing unit of the detector may be arranged to perform a differential measurement on a pattern as detected by the detector, thereby deriving information concerning the differences in propagation between the measurement and reference region from the interference pattern. The interference pattern may be analyzed by a computer program based on a Fast Fourier Transformation algorithm. In the phase part of the Fourier-transformed interference pattern a phase change signal, which corresponds to the differences in propagation between the measurement and reference region, may be derived.

A further detector may be provided having a detection area which extends along the fluidic channel, to detect a scattering of the light along the optical path. There from, a spatial distribution of the propagation characteristics may be derived. Monitoring of light scattered from the sensing surface of the measurement region and/or analyte particles bound on the sensing surface may provide additional information about the binding events. Upon binding of analyte particles on the sensing surface, the intensity of the light scattered from this surface will change, which further could give an indication about the amount of analyte particles bound on the sensing surface. Furthermore, discrimination of analyte particles such as proteins, viruses or bacteria based on their size could be possible because light scattering depends also on the particle size.

In order to align the beam generated by the light source onto multimode interference structure, the system may further comprise a light beam manipulator to manipulate a position of an optical path of the light beam, and a control device to control the light beam manipulator, the control device being arranged to measure an optical pattern as detected by the detector for different positions of the optical path of the light beam, and to control the manipulator so as to obtain a desired optical pattern as detected by the detector.

A core layer preferably having a uniform thickness may be provided not only at the sensing windows, but also in a space between them, which may result in faster reduction/compensation of temperature changes that may occur at any of sensing windows on a readout, which further may result in reduction of temperature drift. The uniform core layer may comprise a Si3N4. In a three-layer waveguide structure, the core layer, which sometimes is also referred to as "guiding layer", is the middle layer that has a higher refractive index than a substrate and cover layers, enabling guiding of the light through such a waveguide structure.

Figure 2:
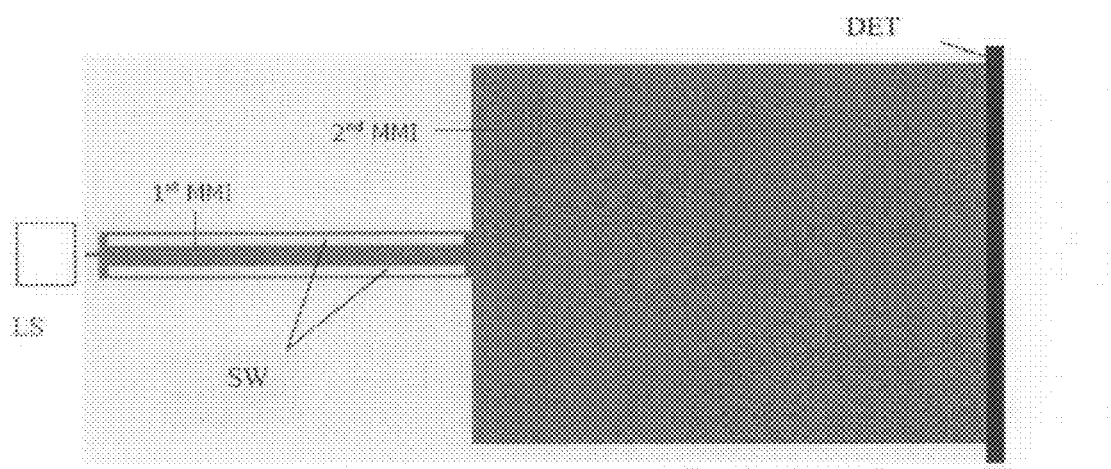
Figure 3:
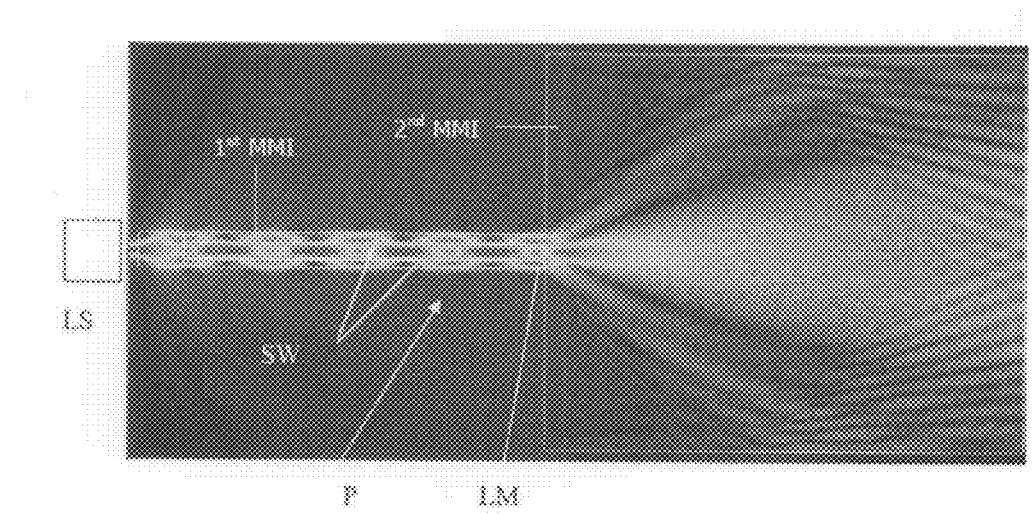

Further advantages, features and effects of the invention will become clear from the appended drawing and description, in which non limiting embodiments of the invention are shown, in which:

FIG. 1 depicts a system comprising a single multimode interference (MMI) structure according to an embodiment of the invention; and FIG. 2 depicts a system comprising dual MMI structures according to another embodiment of the invention, and FIG. 3 depicts a distribution and interference of modes in the MMI according to the embodiment depicted in FIG. 2.

FIG. 1 depicts an MMI structure $1^{st}$ MMI having a light entrance depicted at the left side of the drawing. A beam, such as single mode light beam, entering the $1^{st}$ MMI from a light source LS, such as a laser or laser diode, propagates through the $1^{st}$ MMI in two modes. The first MMI is provided with two sensing windows SW, which may be provided at a top of the planar structure in which the MMI is provided. The fluid (e.g. liquid, gas, suspension, etc) under test is guided over both the sensing windows, thereby the fluid having an effect on the propagation characteristics of the modes. At one of the sensing windows, an antibody or other receptor may be provided in order to interact with the fluid under test, thereby e.g. providing a binding of a particular entity, such as a molecule group, molecule, virus, cell structure, bacterium, etc. Each of the propagation modes travels through the first MMI along the length thereof, thereby interacting with both the measurement and reference windows. A mode distribution in the first MMI is depicted in the left part ($1^{st}$ MMI) section of FIG. 3. As the specific interaction takes place only in the measurement channel, one of the modes is affected more than the other one of the modes, which results in a relative change between the modes at the end of the first MMI. A detector may be positioned here, separately or as an integral part of the planar structure, in order to detect the pattern and derive the change in propagation speed in the measurement channel therefrom.

The system for analysis of a fluid includes a light source LS for radiating a beam of light, an optical path OP for guiding at least part of the beam of light, a fluidic channel FC for guiding the fluid along the optical path, and a detector DET for detecting an optical characteristic of the light having propagated along the optical path, wherein the optical path includes a multimode interference structure 1st MMI the multimode interference structure being arranged for providing a propagation of the beam of light in at least two propagation modes, the detector DET being positioned so as to receive light from each of the at least two propagation modes.

FIG. 2 depicts a second embodiment, wherein a second Multimode interference structure $2^{nd}$ MMI is placed at the end of the first MMI. Due to the larger width of the second MMI, the light from the first MMI propagates through the second MMI in a larger number of propagation modes, while interference between the modes takes place, as is depicted in FIG. 3. As a result, an interference pattern is provided onto the detector, in this example a CCD.

The multimode interference structure may be arranged to allow the at least two propagation modes to propagate in a pattern P of lateral minima and maxima, a propagation length of the first multimode interference structure being dimensioned so as to provide a lateral maximum LM at its end. Thereby an optimum sensitivity may be provided. A processing unit PU of the detector may be arranged to perform a differential measurement on a pattern as detected by the detector, thereby deriving information concerning the differences in propagation between the measurement and reference region from the interference pattern.

In order to align the beam generated by the light source onto multimode interference structure, the system may further comprise a light beam manipulator M to manipulate a position of an optical propagation path of the light beam, and a control device to control the light beam manipulator, the control device CD being arranged to measure an optical pattern as detected by the detector for different positions of the optical propagation path of the light beam, and to control the manipulator so as to obtain a desired optical pattern as detected by the detector.

The invention claimed is:

1. A system for analysis of a fluid, comprising:
   a light source for radiating a beam of light,
   an optical path for guiding at least part of the beam of light,
   a fluidic channel for guiding the fluid along the optical path, and
   a detector for detecting an optical characteristic of the light having propagated along the optical path,
   wherein the optical path comprises a multimode interference structure, the multimode interference structure being arranged for providing a propagation of the beam of light in at least two propagation modes, the detector being positioned so as to receive light from each of the at least two propagation modes, wherein a measurement region and a reference region are provided along a propagation path of the multimode interference structure, the at least two propagation modes of the single beam of light interacting with the measurement region and the reference region.

2. The system according to claim 1, wherein the fluidic channel comprises at least two sensing windows to allow the light to interact with the fluid, one of the sensing windows to act as the reference region, the other to act as the measurement region.

3. The system according to claim 2, wherein the sensing windows extend in parallel along a direction of propagation of the light in the multimode interference structure.

4. The system according to claim 2, wherein an antibody or other receptor is provided along the sensing window which is to act as the measurement region.

5. The system according to claim 1, wherein the multimode interference structure is arranged to allow the at least two propagation modes to propagate in a pattern of lateral minima and maxima, a propagation length of the multimode interference structure being dimensioned so as to provide a lateral maximum at the end of the multimode interference structure.

6. The system according to claim 1, wherein the detector is positioned at an end of the multimode interference structure, so as to provide the light from the at least two propagation modes onto the detector in a spatially distributed manner.

7. The system according claim 1, further comprising a further multimode interference structure which is positioned downstream of the multimode interference structure, the further multimode interference structure having a width exceeding a width of the multimode interference structure to provide multiple propagation modes in the further multimode interference structure, an interference pattern between the multiple propagation modes to be detected by the detector.

8. The system according to claim 1, wherein the light source comprises a single mode light beam source.

9. The system according to claim 1, wherein the multimode interference structure is provided in a chip.

10. The system according to claim 9, wherein the chip further comprises the detector.

11. The system according to claim 1, wherein a processing unit of the detector is arranged to perform a differential measurement on a pattern as detected by the detector.

12. The system according to claim 1, wherein a further detector is provided having a detection area which extends along the fluidic channel, to detect a scattering of the light along the optical path.

13. The system according to claim 1, further comprising a light beam manipulator to manipulate a position of an optical propagation path of the light beam radiated by the light source, and a control device to control the light beam manipulator, the control device being arranged to measure an optical pattern as detected by the detector for different positions of the optical propagation path of the light beam, and to control the light beam manipulator so as to obtain a desired optical pattern as detected by the detector.

14. The system according to claim 1, wherein a uniform core layer of the multimode interference structure is provided.

15. The system according to claim 14, wherein the uniform core layer comprises a $Si_3N_4$.

* * * * *